(12) United States Patent
Ulm, III

(10) Patent No.: US 11,589,936 B1
(45) Date of Patent: Feb. 28, 2023

(54) ROBOTIC SURGICAL SYSTEM

(71) Applicant: Arthur John Ulm, III, Nashville, TN (US)

(72) Inventor: Arthur John Ulm, III, Nashville, TN (US)

( * ) Notice: Subject to any disclaimer, the term of this patent is extended or adjusted under 35 U.S.C. 154(b) by 645 days.

(21) Appl. No.: 16/736,529

(22) Filed: Jan. 7, 2020

Related U.S. Application Data

(60) Provisional application No. 62/789,105, filed on Jan. 7, 2019.

(51) Int. Cl.
| | | |
|---|---|---|
| A61B 34/30 | (2016.01) | |
| A61B 17/22 | (2006.01) | |
| A61B 34/37 | (2016.01) | |
| A61B 34/00 | (2016.01) | |
| A61B 90/00 | (2016.01) | |
| A61B 34/20 | (2016.01) | |

(52) U.S. Cl.
CPC .............. *A61B 34/30* (2016.02); *A61B 17/22* (2013.01); *A61B 34/37* (2016.02); *A61B 34/76* (2016.02); *A61B 2034/2046* (2016.02); *A61B 2034/301* (2016.02); *A61B 2034/303* (2016.02); *A61B 2090/064* (2016.02)

(58) Field of Classification Search
CPC .............. G05G 9/053; G05G 9/04792; G05G 9/04796; G05G 9/04748; G05G 9/04751; H01H 25/06
See application file for complete search history.

(56) References Cited

U.S. PATENT DOCUMENTS

| | | |
|---|---|---|
| 5,431,645 A | 7/1995 | Smith et al. |
| 6,096,004 A | 8/2000 | Meglan et al. |
| 7,063,671 B2 | 6/2006 | Couvillon, Jr. |
| 8,827,948 B2 | 9/2014 | Romo et al. |
| 9,314,306 B2 | 4/2016 | Yu |
| 9,358,072 B2 | 6/2016 | Ullrich |
| 11,058,500 B2 * | 7/2021 | D'Amelio .............. A61B 90/11 |
| 2008/0262480 A1 | 10/2008 | Stahler et al. |
| 2012/0245595 A1 | 9/2012 | Kesavadas et al. |
| 2015/0100069 A1 * | 4/2015 | Inoue ..................... A61B 90/50 606/130 |
| 2016/0213436 A1 * | 7/2016 | Inoue ..................... A61B 34/37 |

* cited by examiner

*Primary Examiner* — Elizabeth Houston
*Assistant Examiner* — Lindsey Bachman
(74) *Attorney, Agent, or Firm* — Shane Cortesi

(57) ABSTRACT

A robotic surgical system is described. In some embodiments, the robotic surgical system includes a physician-side shaft controlled by a physician, the movement of which is tracked by a plurality of physician-side balls and transmitted to a plurality of patient-side balls, which in turn, move a patient-side shaft and attached surgical device, such as a stent retriever.

22 Claims, 4 Drawing Sheets

ROBOTIC SURGICAL SYSTEM

BACKGROUND

Technical Field

The present invention relates to robotic surgical systems, particularly those that provide haptic feedback.

Background of the Invention

Endovascular neurosurgeons typically treat strokes by injecting T-PA or using a thrombectomy device, such as the SOLITAIRE revascularization device (Medtronic, Minneapolis, Minn.) or TREVO retriever (Stryker, Kalamazoo, Mich.). Undersigned inventor is also the designer of the Legacy Ventures LLC dba Vesalio (Nashville, Tenn.) NEVA thrombectomy device, which is described in U.S. Pat. No. 9,173,668, the contents of which are incorporated herein by reference in their entirety, and is currently available commercially in Europe.

Typically thrombectomy devices, particularly stent retrievers, are manipulated by the neurosurgeon in three directions: 1) pulling the device (more particularly the pull wire or other shaft) proximally; 2) pushing the device (more particularly the pull wire or other shaft) distally; and 3) rotating the device (more particularly the pull wire or other shaft) clockwise or counterclockwise relative to the patient-side shaft length/longitudinal axis.

Remote surgical systems are described in, for example, U.S. Patent Publication 2012/0245595, the contents of which are incorporated by reference in their entirety. U.S. Patent Publication 2012/0245595, however, lacks a system that uses at least four balls, which allows the system to track proximal and distal movement and rotation as described below.

Given that neurosurgery is a highly specialized field requiring significant training, there is a need for neurosurgeons to perform the surgery remote from the patient.

BRIEF SUMMARY

The present disclosure provides robotic surgical systems as described herein.

In some embodiments, the robotic surgical system includes a physician-side shaft whose movement may be tracked by a plurality of spherical balls surrounding the physician-side shaft, a patient-side shaft in electronic communication with the physician-side shaft and designed to track the movement of the physician-side shaft and a stent retriever or other distal body attached to the patient-side shaft. The communications between the patient-side and physician-side shafts may be two-way, meaning that in addition to the physician-side shaft controlling movement of the patient-side shaft, the patient-side shaft may provide haptic feedback to the physician-side shaft.

In some embodiments, the present disclosure provides a robotic surgical system comprising a physician-side shaft having a physician-side shaft proximal end, a physician-side shaft distal end, a physician-side shaft length extending from the physician-side shaft proximal end to the physician-side shaft distal end, the physician-side shaft configured to be moved by a physician in the proximal direction, in the distal direction, and to rotate clockwise and counterclockwise relative to the physician-side shaft length. Optionally, the robotic surgical system further comprises a first physician-side set of a plurality of spherical balls surrounding the physician-side shaft, the plurality of spherical balls in the first physician-side set of a plurality of spherical balls configured to move in response to movement of the physician-side shaft. Optionally, the robotic surgical system further comprises a physician-side sensor configured to measure movement of the first physician-side set of plurality of spherical balls. Optionally, the robotic surgical system further comprises a physician-side transmitter configured to transmit signals received from the physician-side sensor. Optionally, the robotic surgical system further comprises a patient-side receiver configured to receive signals transmitted by the physician-side transmitter. Optionally, the robotic surgical system further comprises a patient-side shaft having a patient-side shaft proximal end, a patient-side shaft distal end, a patient-side shaft length extending from the patient-side shaft proximal end to the pull distal end, the patient-side shaft configured to move in the proximal direction, in the distal direction, and to rotate clockwise and counterclockwise relative to the patient-side shaft length in response to signals received by the patient-side receiver. Optionally, the robotic surgical system further comprises a distal body comprising a distal body interior, a distal body perimeter, a distal body proximal end connected (directly or indirectly) to the patient-side shaft, a distal body distal end, a distal body length extending from the distal body proximal end to the distal body distal end, and a distal body height and width perpendicular to the distal body length, the distal body comprising a framework formed by a plurality of memory metal strips, wherein the distal body has a relaxed state wherein the distal body has a first height and a first width, and a collapsed state wherein the distal body has a second height and a second width, the second height of the distal body less than the first height of the distal body, the second width of the distal body less than the first width of the distal body. Optionally, the robotic surgical system further comprises a patient-side force applicator configured to move the patient-side shaft in the proximal direction, in the distal direction, and to rotate clockwise and counterclockwise relative to the patient-side shaft length in response to signals received by the patient-side receiver. Optionally, the patient-side force applicator comprises a motor. Optionally, the patient-side force applicator comprises a magnet. Optionally, the patient-side force applicator comprises a first patient-side set of a plurality of spherical balls surrounding the patient-side shaft, the plurality of spherical balls in the first patient-side set of plurality of spherical balls configured to move the patient-side shaft in the proximal direction, in the distal direction, and to rotate the patient-side shaft clockwise and counterclockwise relative to the patient-side shaft length in response to signals received by the patient-side receiver. Optionally, the patient-side force applicator further comprises a second patient-side set of a plurality of spherical balls surrounding the patient-side shaft, the plurality of balls in the second patient-side set of plurality of spherical balls located distal to the first patient-side set of plurality of spherical balls and configured to move the patient-side shaft in the proximal direction, in the distal direction, and to rotate the patient-side shaft clockwise and counterclockwise relative to the patient-side shaft length in response to signals received by the patient-side receiver. Optionally, the first patient-side set of a plurality of spherical balls comprises at least four spherical balls. Optionally, the patient-side shaft is a wire. Optionally, the wire comprises a variable height and width and optionally, the maximum width and maximum height of the wire is less than the wire's length. Optionally, the physician-side shaft is a wire. Optionally, the robotic surgical system further comprises a patient-side sensor configured to, for example, measure load on the patient-side shaft. Optionally, the robotic surgical system further comprises a patient-side transmitter configured to transmit signals received from the patient-side sensor, a physician-side receiver configure to receive signals transmitted by the patient-side transmitter, and a physician-side force applicator configured to move the physician-side shaft in the proximal direction, in the distal direction, and to rotate the physician-side shaft clockwise and counterclockwise relative to the physician-side shaft length in response to signals received by the physician-side receiver. Optionally, the robotic surgical system further comprises a second physician-side set of a plurality of spherical balls surrounding the physician-side shaft, the plurality of balls in the second physician-side set of plurality of spherical balls located proximal or distal to the first physician-side set of plurality of spherical balls and configured to move the physician-side shaft in the proximal direction, in the distal direction, and to rotate the physician-side shaft clockwise and counterclockwise relative to the physician-side shaft length in response to signals received by the physician-side receiver. Optionally, the second physician-side set of a plurality of spherical balls comprises at least four spherical balls. Optionally, the robotic surgical system further comprises a plurality of ball housings comprising partially-spherical cavities configured to partially house the plurality of spherical balls of the first physician-side set of plurality of spherical balls. Optionally, each housing comprises two halves, each halve partially forming a partially-spherical cavity. Optionally, the physician-side shaft and the patient-side shaft are in remote locations.

In still further embodiments, the present disclosure provides a method of removing a blood clot from a blood vessel of an animal the method comprising the steps of: a) providing the robotic surgical system; b) positioning a catheter comprising the distal body in the blood vessel; c) deploying the distal body from the catheter and allowing the height and width of the distal body to increase; d) capturing the blood clot with the distal body; and e) pulling on the physician-side shaft proximally; f) moving the first set of spherical balls in response to pulling on the physician-side shaft; g) using the physician-side sensor to measure movement of the first set of plurality of spherical balls; h) transmitting signals received from the physician-side sensor from the physician-side transmitter to the patient-side receiver; and i) moving the patient-side shaft and the distal body in the proximal direction in response to signals received by the patient-side receiver. The robotic surgical system may have one or more features described above. Additional methods of use are also described herein.

BRIEF DESCRIPTION OF THE DRAWINGS

as shown in FIG. 1, the distal body/stent retriever is in the patient and the system is being controlled by a remote physician.

DETAILED DESCRIPTION

Figure 1:
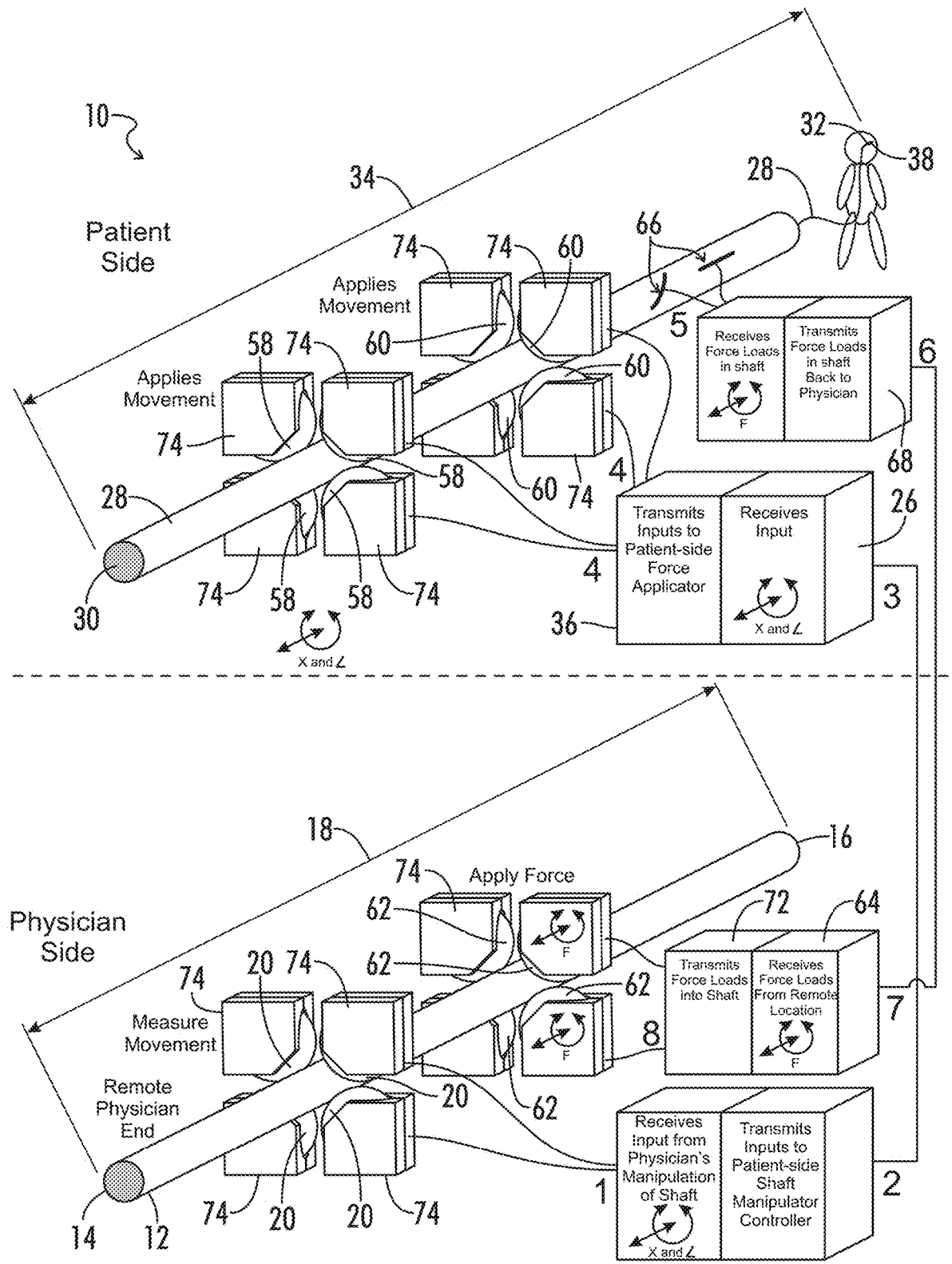
FIG. 1 illustrates a schematic view of one embodiment of the robotic surgical system of the present invention.
Figure 2:
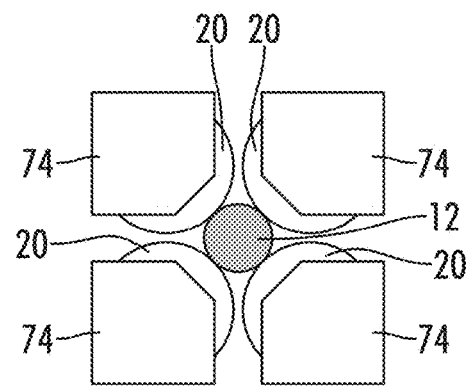
FIG. 2 illustrates a front elevation view of the physician-side shaft and first physician-side set of plurality of balls (and associated housings) of FIG. 1.
Figure 3:
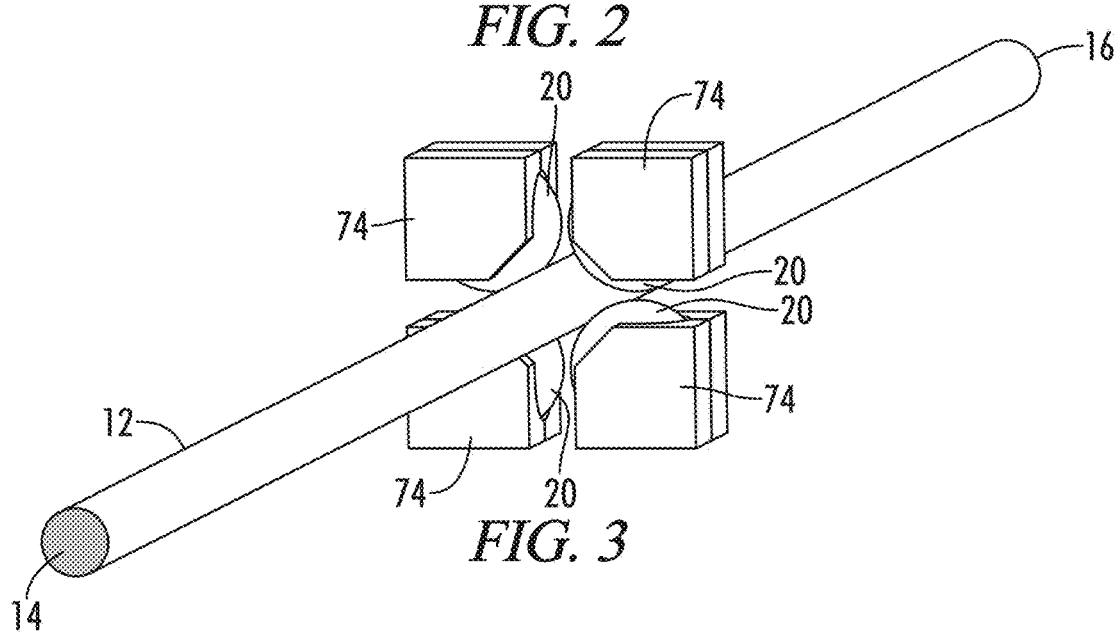
FIG. 3 illustrates a side perspective view of the physician-side shaft and first physician-side set of plurality of balls (and associated housings) of FIG. 2.
Figure 4:
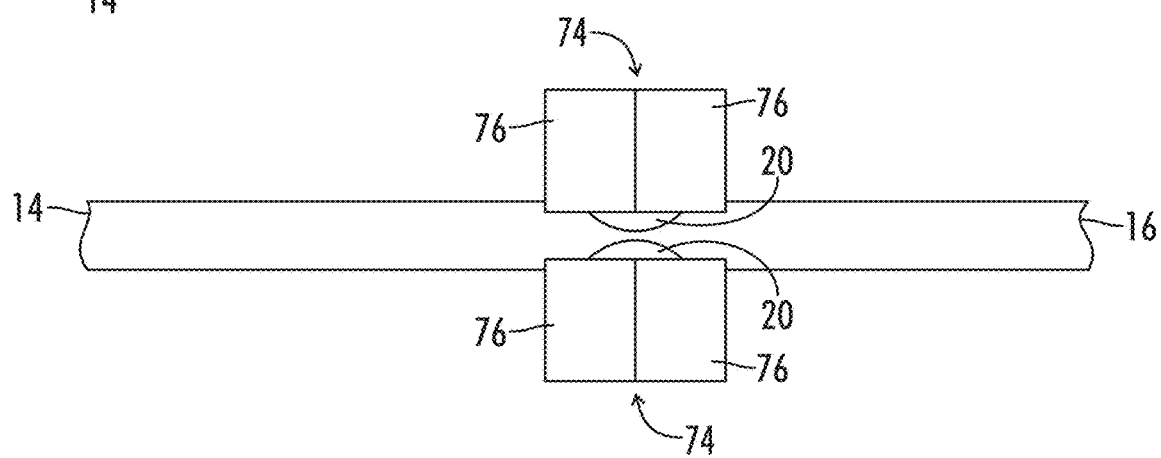
FIG. 4 illustrates a top plan view of the physician-side shaft and first physician-side set of plurality of balls (and associated housings) of FIG. 2.

With reference to FIGS. 1-6 the present invention provides a robotic surgical system, designated by the numeral 10. In the drawings, not all reference numbers are included in each drawing for the sake of clarity.

Referring to FIGS. 1-6, the robotic surgical system 10 may include a physician-side shaft 12 (e.g., a metallic wire) having a physician-side shaft proximal end 14, a physician-side shaft distal end 16, a physician-side shaft length 18 extending from the physician-side shaft proximal end 14 to the physician-side shaft distal end 16. The physician-side shaft 12 is configured to be moved by a physician in the proximal direction, in the distal direction, and to rotate clockwise and counterclockwise relative to the physician-side shaft length/longitudinal axis 18. The physician-side shaft 12 may have a diameter and other characteristics similar to the patient-side shaft 28 (described below) to provide a more realistic experience. Alternatively, the physician-side shaft 12 may be wider than the patient-side shaft 28. Patient-side shafts 28 (such as pull wires) are described in U.S. Patent Publication 2018/0296235, the entire contents of which are hereby incorporated by reference.

The robotic surgical system 10 may further include a first physician-side set of a plurality of spherical balls 20 (e.g., at least four spherical balls) surrounding the physician-side shaft 12. The plurality of spherical balls 20 in the first physician-side set of plurality of spherical balls are configured to move in response to movement of the physician-side shaft 12. Preferably, at least four spherical balls are used in order to track proximal and distal movement as well as rotation of the physician-side shaft 12. Preferably, all balls 20, 58, 60 and 62 described herein are spherical in shape.

The robotic surgical system 10 may further include a physician-side sensor 22 (and associated processor) configured to measure movement of the first physician-side set of a plurality of spherical balls 20.

The robotic surgical system 10 may further include a physician-side transmitter 24 configured to transmit signals received from the physician-side sensor 22. It will be understood that any components described herein can combined. Thus, for example, the physician-side sensor 22, which may for example include stress and strain gauges 66, may also contain the physician-side transmitter 24.

The robotic surgical system 10 may further include a patient-side receiver 26 configured to receive signals transmitted by the physician-side transmitter 24.

The robotic surgical system 10 may further include a patient-side shaft 28 (e.g., metallic wire) having a patient-side shaft proximal end 30, a patient-side shaft distal end 32, a patient-side shaft length 34 extending from the patient-side shaft proximal end 30 to the patient-side shaft distal end 32, the patient-side shaft 28 configured to move in the proximal direction, in the distal direction, and to rotate clockwise and counterclockwise relative to the patient-side shaft length 34 in response to signals received by the patient-side receiver 26. As mentioned above, patient-side shafts 28 (such as pull wires) are described in U.S. Patent Publication 2018/0296235. Optionally, the patient-side shaft 28 has a variable width and height, and is narrower at the distal end 32 than at the proximal end 30, to enable the patient-side shaft 28 to be moved by the plurality of spherical balls 58 in the first set of patient-side spherical balls.

Figure 7:
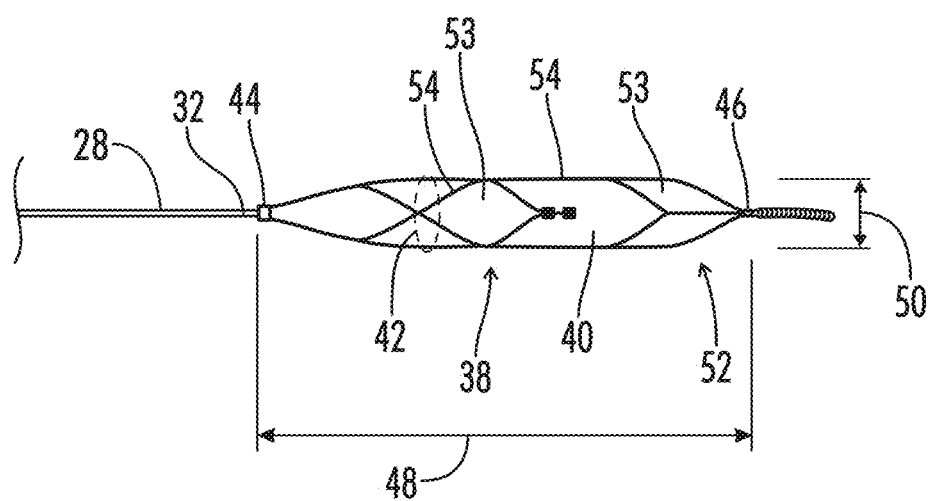
FIG. 7 illustrates a distal body for use with a robotic surgical system of the present invention.

The robotic surgical system 10 may further include a surgical instrument. In some embodiments, as shown in FIG. 7, the surgical instrument is a distal body 38 comprising a distal body interior 40, a distal body perimeter 42, a distal body proximal end 44 connected to the patient-side shaft 28, a distal body distal end 46, a distal body length 48 extending from the distal body proximal end 44 to the distal body distal end 46, and a distal body height 50 and width perpendicular to the distal body length 48. The distal body 38 may comprise a distal body framework 52 formed by a plurality of cells 53 formed by a plurality of memory metal strips 54. Optionally, the distal body 38 has a relaxed state wherein the distal body 38 has a first height and a first width, and a collapsed state wherein the distal body 38 has a second height and a second width, the second height of the distal body 38 less than the first height of the distal body 38, the second width of the distal body 38 less than the first width of the distal body 38. In a preferred embodiment, the distal body 38 is a stent retriever. Stent retrievers are described in U.S. Patent Publication 2018/0296235 and include the NeVa stent retriever (Legacy Ventures LLC, Nashville, Tenn.). Other examples of stent retrievers include the SOLITAIRE revascularization device (Medtronic, Minneapolis, Minn.) and TREVO retriever (Stryker, Kalamazoo, Mich.).

Optionally, the robotic surgical system 10 further includes a patient-side force applicator 36 configured to move the patient-side shaft 28 in the proximal direction, in the distal direction, and to rotate the patient-side shaft 28 clockwise and counterclockwise relative to the patient-side shaft length 34 in response to signals received by the patient-side receiver 26. For example, the patient-side force applicator 36 may comprise a motor or a magnet. The patient side force applicator 36 also may comprise a first patient-side set of a plurality of spherical balls 58 (e.g., at least four spherical balls) surrounding the patient-side shaft 28, the first patient-side set of plurality of spherical balls 58 configured to move the patient-side shaft 28 in the proximal direction, in the distal direction, and to rotate the patient-side shaft 28 clockwise and counterclockwise relative to the patient-side shaft length 34 in response to signals received by the patient-side receiver 26. More particularly, the plurality of spherical balls 58 may apply electrical/magnetic, optical or mechanical force to move the patient-side shaft 28. For example, the aforementioned motor may be used to apply force to the patient-side shaft 28 via the first patient-side set of a plurality of spherical balls 58.

Optionally, the robotic surgical system 10 further comprises a second patient-side set of a plurality of spherical balls 60 (e.g., at least four spherical balls) surrounding the patient-side shaft 28, the second patient-side set of plurality of spherical balls 60 located distal to the first patient-side set of plurality of spherical balls 58 and configured to also move the patient-side shaft 28 in the proximal direction, in the distal direction, and to rotate the patient-side shaft 28 clockwise and counterclockwise relative to the patient-side shaft length 34 in response to signals received by the patient-side receiver 26. A reason for the second patient-side set of plurality of spherical balls 60 is that it may be necessary, from a stability standpoint, to have two sets of patient-side plurality of spherical balls 58 and 60 to move the patient-side shaft 28.

Optionally, the robotic surgical system 10 further comprises a patient-side sensor 66 (and associated processor) configured to measure load on the patient-side shaft 28, shown as stress and strain gauges in FIG. 1. Optionally, the robotic surgical system 10 further comprises a patient-side transmitter 68 configured to transmit signals received from the patient-side sensor 66, a physician-side receiver 64 configured to receive signals transmitted by the patient-side transmitter 68, and a physician-side force applicator 72 configured to move the physician-side shaft 12 in the proximal direction, in the distal direction, and to rotate the physician-side shaft 12 clockwise and counterclockwise relative to the physician-side shaft length 18 in response to signals received by the physician-side receiver 64 in order to provide haptic feedback to the physician. More particularly, the robotic surgical system 10 may further comprises a second physician-side set of a plurality of spherical balls 62 (e.g., at least four spherical balls) surrounding the physician-side shaft 12, the second physician-side set of plurality of spherical balls 62 located proximal or distal to the first physician-side set of plurality of spherical balls 20 and configured to move the physician-side shaft 12 in the proximal direction, in the distal direction, and to rotate the physician-side shaft 12 clockwise and counterclockwise relative to the physician-side shaft length 18 in response to signals received by the physician-side receiver 64.

Figure 5:
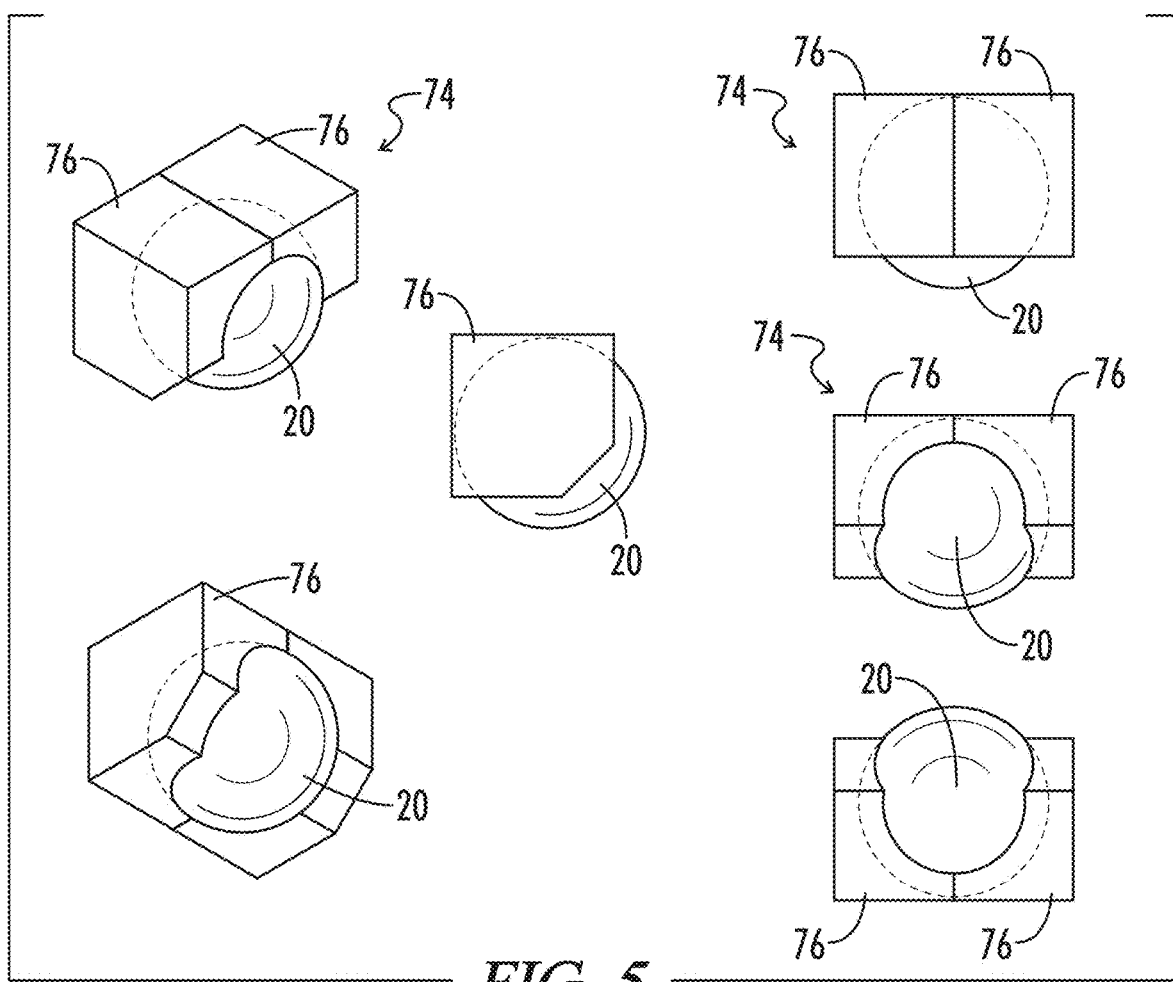
FIG. 5 illustrates a plurality of views showing how each housing of FIG. 2 comprises two halves that form a partially spherical cavity for retaining a ball.
Figure 6:
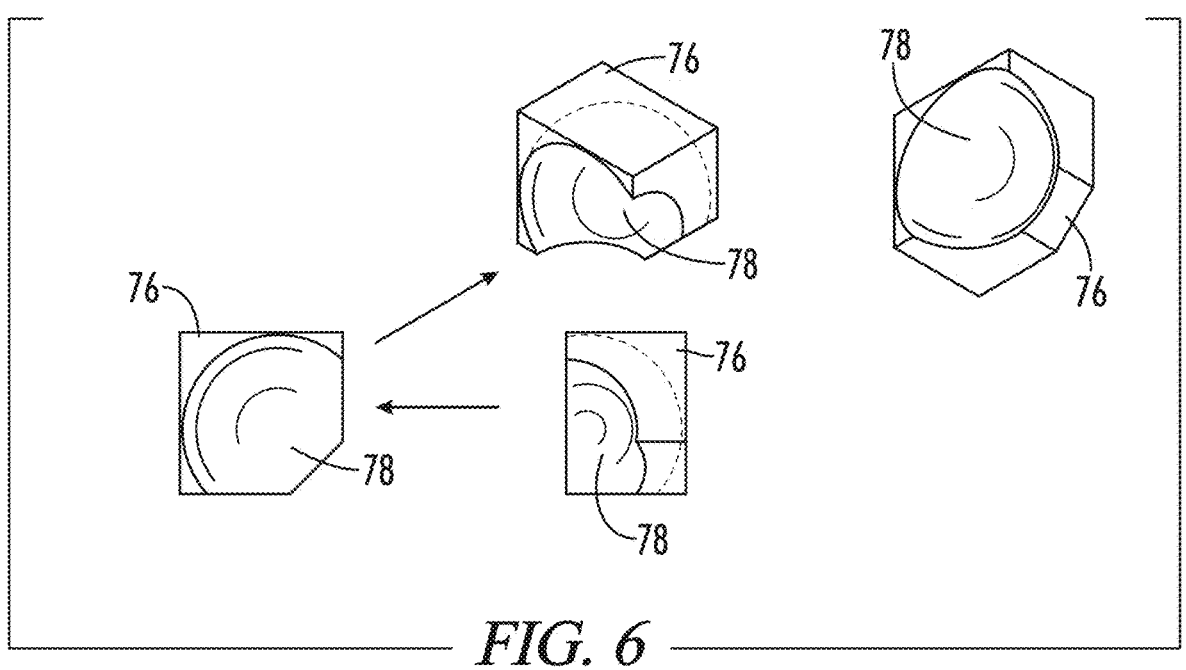
FIG. 6 illustrates a plurality of views of a half of a housing of FIG. 2.

Optionally, the robotic surgical system 10 further comprises a plurality of ball housings 74 comprising partially-spherical cavities 78 configured to partially house the plurality of spherical balls 20, 58, 60 and 62 described herein, as best seen in FIGS. 5 and 6. The ball housings 74 and the plurality of spherical balls 20, 58, 60 and 62 may function similar to a computer mouse. Optionally, each ball housing 74 is comprised of two halves 76, each half partially forming a partially-spherical cavity 78.

Optionally, the physician-side shaft 12 and the patient-side shaft 28 are in different locations, allowing the physician to work remotely from a patient located in a hospital operating room.

Optionally, the robotic surgical system 10 is used in removing a blood clot from a blood vessel of an animal that comprises the steps of: a) providing the robotic surgical system 10; b) positioning a catheter comprising the distal body 30 in the blood vessel, as described for example in US Patent Publication 2018/0296235; c) deploying the distal body 30 from the catheter and allowing the height and width of the distal body 30 to increase; d) capturing the blood clot with the distal body; 30 e) pulling on the physician-side shaft 12 proximally; f) moving at least one spherical ball of the first physician-side set 20 of spherical balls in response to pulling on the physician-side shaft 12 (i.e., capturing the physician's pull movement in step e); g) using the physician-side sensor 22 to measure movement of the at least one spherical ball; h) transmitting signals received from the physician-side sensor 22 from the physician-side transmitter 24 to the patient-side receiver 26; i) moving the patient-side shaft 28 and the attached distal body 30 in the proximal direction in response to signals received by the patient-side receiver 26. In other words, physician-side movement at step f) is translated to the patient-side procedure at step i), allowing the physician to remotely control the surgery.

Referring to FIG. 1, at Step 1, the physician moves the physician-side shaft 12 (proximally, distally or rotating clockwise or counterclockwise), which in turn moves the plurality of spherical balls in the first physician-side set of plurality of spherical balls 20, the movement of which is tracked by the physician-side sensor 22. At Steps 2-3, this movement information is transmitted from the physician-side transmitter 24 to the patient-side receiver 26. At Step 4, this movement information is translated to the plurality of spherical balls in the first and second set of patient-side spherical balls 58 and 60, which in turn move the patient-side shaft 28 to mimic the physician's movement of the physician-side shaft 12. At Step 5, feedback from the patient-side shaft 28 is sensed by stress and strain gauges 66. At Steps 6 and 7, this feedback information is transmitted from the patient-side transmitter 68 to the physician-side receiver 64. At Step 8, this feedback information is translated to the plurality of spherical balls in the second physician-side set of a plurality of spherical balls 62, which in turn move the physician-side shaft 12 thereby providing haptic feedback to the physician.

PART LIST

| | |
|---|---|
| System | 10 |
| physician-side shaft | 12 |
| physician-side shaft proximal end | 14 |
| physician-side shaft distal end | 16 |
| physician-side shaft length | 18 |
| first physician-side set of a plurality of spherical balls | 20 |
| physician-side sensor | 22 |
| physician-side transmitter | 24 |
| patient-side receiver | 26 |
| patient-side shaft | 28 |
| patient-side shaft proximal end | 30 |
| patient-side shaft distal end | 32 |
| patient-side shaft length | 34 |
| patient-side force applicator | 36 |
| distal body | 38 |
| distal body interior | 40 |
| distal body perimeter | 42 |
| distal body proximal end | 44 |
| distal body distal end | 46 |
| distal body length | 48 |
| distal body height | 50 |
| distal body framework | 52 |
| plurality of cells | 53 |
| plurality of memory metal strips | 54 |
| first patient-side set of a plurality of spherical balls | 58 |
| second patient-side set of a plurality of spherical balls | 60 |
| second physician-side set of a plurality of spherical balls | 62 |
| physician-side receiver | 64 |
| patient-side sensor | 66 |
| patient-side transmitter | 68 |
| physician-side force applicator | 72 |
| ball housings | 74 |
| ball housing halves | 76 |
| ball housing cavities | 78 |

Having now described the invention in accordance with the requirements of the patent statutes, those skilled in the art will understand how to make changes and modifications to the disclosed embodiments to meet their specific requirements or conditions. Changes and modifications may be made without departing from the scope and spirit of the invention. In addition, the steps of any method described herein may be performed in any suitable order and steps may be performed simultaneously if needed.

Terms of degree such as "generally", "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies. In addition, the steps of the methods described herein can be performed in any suitable order, including simultaneously. It is understood that use of the singular embraces the plural and vice versa.

What is claimed is:

1. A robotic surgical system comprising:
   a physician-side shaft having a physician-side shaft proximal end, a physician-side shaft distal end, a physician-side shaft length extending from the physician-side shaft proximal end to the physician-side shaft distal end, the physician-side shaft configured to be moved by a physician in the proximal direction, in the distal direction, and to rotate clockwise and counterclockwise relative to the physician-side shaft length;
   a first physician-side set of at least four spherical balls surrounding the physician-side shaft, the at least four spherical balls in the first physician-side set of at least four spherical balls configured to move in response to movement of the physician-side shaft;
   a physician-side sensor configured to measure movement of the first physician-side set of at least four spherical balls;
   a physician-side transmitter configured to transmit signals received from the physician-side sensor;
   a patient-side receiver configured to receive signals transmitted by the physician-side transmitter;
   a patient-side shaft having a patient-side shaft proximal end, a patient-side shaft distal end, a patient-side shaft length extending from the patient-side shaft proximal end to the patient-side shaft distal end, the patient-side shaft configured to move in the proximal direction, in the distal direction, and to rotate clockwise and counterclockwise relative to the patient-side shaft length in response to signals received by the patient-side receiver; and
   a distal body comprising a distal body interior, a distal body perimeter, a distal body proximal end connected to the patient-side shaft, a distal body distal end, a distal body length extending from the distal body proximal end to the distal body distal end, and a distal body height and width perpendicular to the distal body length, the distal body comprising a distal body framework formed by a plurality of memory metal strips, wherein the distal body has a relaxed state wherein the distal body has a first height and a first width, and a collapsed state wherein the distal body has a second height and a second width, the second height of the distal body less than the first height of the distal body, the second width of the distal body less than the first width of the distal body.

2. The robotic surgical system of claim 1 further comprising a patient-side force applicator configured to move the patient-side shaft in the proximal direction, in the distal direction, and to rotate the patient-side shaft clockwise and counterclockwise relative to the patient-side shaft length in response to signals received by the patient-side receiver.

3. The robotic surgical system of claim 2 wherein the patient-side force applicator comprises a motor.

4. The robotic surgical system of claim 2 wherein the patient-side force applicator comprises a magnet.

5. The robotic surgical system of claim 2 wherein the patient-side force applicator further comprises a first patient-side set of at least four spherical balls surrounding the patient-side shaft, the at least four spherical balls in the first patient-side set of at least four spherical balls configured to move the patient-side shaft in the proximal direction, in the distal direction, and to rotate the patient-side shaft clockwise and counterclockwise relative to the patient-side shaft length in response to signals received by the patient-side receiver.

6. The robotic surgical system of claim 5 wherein the patient-side force applicator further comprises a second patient-side set of at least four spherical balls surrounding the patient-side shaft, the at least four spherical balls in the second patient-side set of at least four spherical balls located distal to the first patient-side set of at least four spherical balls and configured to move the patient-side shaft in the proximal direction, in the distal direction, and to rotate the patient-side shaft clockwise and counterclockwise relative to the patient-side shaft length in response to signals received by the patient-side receiver.

7. The robotic surgical system of claim 1 wherein the patient-side shaft is a wire.

8. The robotic surgical system of claim 7 wherein the wire comprises a variable height and width, and further wherein the maximum height and maximum width of the wire is less than the length of the wire.

9. The robotic surgical system of claim 1 wherein the physician-side shaft is a wire.

10. The robotic surgical system of claim 1 wherein the robotic surgical system further comprises a patient-side sensor configured to measure load on the patient-side shaft.

11. The robotic surgical system of claim 10 wherein the robotic surgical system further comprises a patient-side transmitter configured to transmit signals received from the patient-side sensor, a physician-side receiver configured to receive signals transmitted by the patient-side transmitter, and a physician-side force applicator configured to move the physician-side shaft in the proximal direction, in the distal direction, and to rotate the physician-side shaft clockwise and counterclockwise relative to the physician-side shaft length in response to signals received by the physician-side receiver.

12. The robotic surgical system of claim 11 wherein the robotic surgical system further comprises a second physician-side set of at least four spherical balls surrounding the physician-side shaft, the at least four spherical balls in the second physician-side set of at least four spherical balls located proximal or distal to the first physician-side set of at least four spherical balls and configured to move the physician-side shaft in the proximal direction, in the distal direction, and to rotate the physician-side shaft clockwise and counterclockwise relative to the physician-side shaft length in response to signals received by the physician-side receiver.

13. The robotic surgical system of claim 1 further comprising a plurality of ball housings comprising partially-spherical cavities configured to partially house the at least four spherical balls of the first physician-side set of plurality of at least four spherical balls.

14. The robotic surgical system of claim 13 wherein each housing is comprised of two halves, each half partially forming a partially-spherical cavity.

15. The robotic surgical system of claim 1 wherein the physician-side shaft and the patient-side shaft are in different locations.

16. The robotic surgical system of claim 1 wherein the framework is comprised of a plurality of cells formed by the plurality of memory metal strips.

17. A method of removing a blood clot from a blood vessel of an animal the method comprising the steps of:
 a) providing the robotic surgical system of claim 1;
 b) positioning a catheter comprising the distal body in the blood vessel;
 c) deploying the distal body from the catheter and allowing the height and width of the distal body to increase;
 d) capturing the blood clot with the distal body;
 e) pulling on the physician-side shaft proximally;
 f) moving at least one spherical ball in the first physician-side set of at least four spherical balls in response to pulling on the physician-side shaft;
 g) using the physician-side sensor to measure movement of the at least one spherical ball in the first physician-side set of at least four spherical balls;
 h) transmitting signals received from the physician-side sensor from the physician-side transmitter to the patient-side receiver; and
 i) moving the patient-side shaft and the distal body in the proximal direction in response to signals received by the patient-side receiver.

18. The method of claim 17 further comprising the steps of:
 j) rotating the physician-side shaft clockwise or counterclockwise;
 k) moving at least one spherical ball in the first physician-side set of at least four spherical balls in response to rotating the physician-side shaft;
 l) using the physician-side sensor to measure movement of the at least one spherical ball of step k);
 m) transmitting signals received from the physician-side sensor from the physician-side transmitter to the patient-side receiver; and
 n) rotating the patient-side shaft in response to signals received by the patient-side receiver.

19. A method of using a robotic surgical system comprising:
 a) providing robotic surgical system comprising:
  i) a physician-side shaft having a physician-side shaft proximal end, a physician-side shaft distal end, a physician-side shaft length extending from the physician-side shaft proximal end to the physician-side shaft distal end, the physician-side shaft configured to be moved by a physician in the proximal direction, in the distal direction, and to rotate clockwise and counterclockwise relative to the physician-side shaft length;
  ii) a first physician-side set of at least four spherical balls surrounding the physician-side shaft, the at least four spherical balls in the first physician-side set of at least four spherical balls configured to move in response to movement of the physician-side shaft;
  iii) a physician-side sensor configured to measure movement of the first physician-side set of at least four spherical balls;
  iv) a physician-side transmitter configured to transmit signals received from the physician-side sensor;
  v) a patient-side receiver configured to receive signals transmitted by the physician-side transmitter;
  vi) a patient-side shaft having a patient-side shaft proximal end, a patient-side shaft distal end, a patient-side shaft length extending from the patient-side shaft proximal end to the patient-side shaft distal end, the patient-side shaft configured to move in the proximal direction, in the distal direction, and to rotate clockwise and counterclockwise relative to the patient-side shaft length in response to signals received by the patient-side receiver;
  vii) patient-side force applicator configured to move the patient-side shaft in the proximal direction, in the distal direction, and to rotate the patient-side shaft clockwise and counterclockwise relative to the patient-side shaft length in response to signals received by the patient-side receiver; and
  viii) a surgical instrument connected to the patient-side shaft;

b) moving the physician-side shaft;

c) moving at least one spherical ball of the first physician-side set of four spherical balls in response to step b);

d) measuring movement of the at least one spherical ball in step c);

e) sending signals from the physician-side sensor to the physician-side transmitter;

f) sending signals from the physician-side transmitter to the patient-side receiver; and g) moving the patient-side shaft and the surgical body using the patient-side force applicator.

20. The method of claim 19 further comprising the step of h) providing haptic feedback to the physician-side shaft after step g).

21. The method of claim 19, wherein the robotic surgical system further comprises a patient-side sensor, wherein the robotic surgical system further comprises a patient-side transmitter configured to transmit signals received from the patient-side sensor, a physician-side receiver configured to receive signals transmitted by the patient-side transmitter, and a physician-side force applicator configured to move the physician-side shaft in the proximal direction, in the distal direction, and to rotate the physician-side shaft clockwise and counterclockwise relative to the physician-side shaft length in response to signals received by the physician-side receiver, and the method further comprises h) sending signals from the patient-side sensor to the patient-side transmitter; i) sending signals from the patient-side transmitter to the physician-side receiver; and j) moving the physician-side shaft using the physician-side force applicator.

22. The method of claim 19 wherein the surgical instrument is a distal body comprising a distal body interior, a distal body perimeter, a distal body proximal end connected to the patient-side shaft, a distal body distal end, a distal body length extending from the distal body proximal end to the distal body distal end, and a distal body height and width perpendicular to the distal body length, the distal body comprising a distal body framework formed by a plurality of memory metal strips, wherein the distal body has a relaxed state wherein the distal body has a first height and a first width, and a collapsed state wherein the distal body has a second height and a second width, the second height of the distal body less than the first height of the distal body, the second width of the distal body less than the first width of the distal body.

* * * * *